US008067053B2

(12) United States Patent
Laskin et al.

(10) Patent No.: US 8,067,053 B2
(45) Date of Patent: Nov. 29, 2011

(54) METHOD FOR SELECTIVE IMMOBILIZATION OF MACROMOLECULES ON SELF ASSEMBLED MONOLAYER SURFACES

(75) Inventors: Julia Laskin, Richland, WA (US); Peng Wang, Billerica, MA (US)

(73) Assignee: Battelle Memorial Institute, Richland, WA (US)

( * ) Notice: Subject to any disclaimer, the term of this patent is extended or adjusted under 35 U.S.C. 154(b) by 580 days.

(21) Appl. No.: 12/151,945

(22) Filed: May 9, 2008

(65) Prior Publication Data

US 2009/0280264 A1  Nov. 12, 2009

(51) Int. Cl.
*B05D 3/00* (2006.01)
(52) U.S. Cl. ....... 427/2.11; 427/533; 427/536; 435/402; 436/518; 436/528
(58) Field of Classification Search .................. None
See application file for complete search history.

(56) References Cited

U.S. PATENT DOCUMENTS

2003/0226963 A1  12/2003  Cooks et al.
2006/0071665 A1  4/2006  Blake et al.

OTHER PUBLICATIONS

Wang et al., Covalent immobilization of peptides on self-assembled monolayer surfaces using soft-landing of mass-selected ions, Jun. 2007, 129: pp. 8682-8683.*
Alvarez et al., Soft landing of peptides onto self-assembled monolayer surfaces, 2006, J Phys Chem, 110: pp. 1678-1687.*
Alvarez, et al., Preparation and in Situ Characterization of Surfaces Using Soft Landing in a Fourier transform Ion Cyclotron resonance Mass Spectrometer, Anal. Chem, vol. 77, 2005, pp. 3452-3460.
Alavarez, Jormarie, Soft-Landing of Peptides onto Self-Assembled Monolayer Surfaces, J. Phys. Chem. A, vol. 110, 2006, pp. 1678-1687.
Gologan, et al., Ion/surface reactions and ion soft-landing, Phys. Chem. Chem. Phys., vol. 7, 2005, pp. 1490-1500.
Hadjar, et al, Design and Performance of an Instrument for Soft Landing of Biomolecular Ions on Surfaces, Analytical Chemistry, vol. 79, No. 17, Sep. 1, 2007, pp. 6566-6574.
Hadjar et al., First Observation of Charge Reduction and Desorption Kinetics of Multiply Protonated Peptides Soft Landed onto Self-Assembled Monolayer Surfaces, J. Phys. Chem. C, vol. 111, 2007, pp. 18220-18225.
Wang et al., Covalent Immobilization of Peptides on Self-Assembled Monolayer Surfaces using Soft-Landing of Mass-Selected Ions, J. Am. Chem. Soc., vol. 129, 2007, pp. 8682-8683.
Lahiri et al., A Strategy for the Generation of Surfaces Presenting Ligands for Studies of Binding Based on an Active Ester as a Common Reactive Intermediate: A Surface Plasmon Resonance Study, Anal. Chem, vol. 71, 1999, pp. 777-790.

(Continued)

*Primary Examiner* — N. Yang
(74) *Attorney, Agent, or Firm* — James D. Matheson (57) ABSTRACT

Disclosed is a method for selective chemical binding and immobilization of macromolecules on solid supports in conjunction with self-assembled monolayer (SAM) surfaces. Immobilization involves selective binding of peptides and other macromolecules to SAM surfaces using reactive landing (RL) of mass-selected, gas phase ions. SAM surfaces provide a simple and convenient platform for tailoring chemical properties of a variety of substrates. The invention finds applications in biochemistry ranging from characterization of molecular recognition events at the amino acid level and identification of biologically active motifs in proteins, to development of novel biosensors and substrates for stimulated protein and cell adhesion.

26 Claims, 3 Drawing Sheets

OTHER PUBLICATIONS

Laskin et al., Charge retention by peptide ions soft-landed onto self-assembled monolayer surfaces, Science Direct, International Journal of Mass Spectrometry, vol. 265, 2007, pp. 237-243.

Wang et al., Reactive landing of peptide ions on self-assembled monolayer surfaces: an alternative approach for covalent immobilization of peptides on surfaces, Physical Chemistry Chemical Physics, vol. 10, 2008, pp. 1512-1522.

Laskin et al., Soft-landing of peptide ions onto self-assembled monolayer surfaces: an overview, Physical Chemistry Chemical Physics, vol. 10, No. 8, Feb. 28, 2008, pp. 1069-1216.

Volny et al., Preparative Soft and Reactive Landing of Gas-Phase Ions on Plasma-Treated Metal Surfaces, Anal. Chem., vol. 77, 2005, pp. 4846-4853.

Volny et al., Preparative Soft and Reactive Landing of Multiply Charged Protein Ions on a Plasma-Treated Metal Surface, Ana. Chem., vol. 77, 2005, pp. 4890-4896.

Wagner et al., Covalent Immobilization of Native Biomolecules onto Au(111) via N-Hydroxysuccinimide Ester Functionalized Self-Assembled Monolayers for Scanning Probe Microscopy, Biophysical Journal, vol. 70, May 1996, pp. 2052-2066.

* cited by examiner

SEQUENCE LISTING

<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: cyclic pentapeptide, synthetically derived
<220> FEATURE:
<221> NAME/KEY: PEPTIDE
<222> LOCATION: (1)..(5)
<223> OTHER INFORMATION: Binds to NHS-SAM surface through amino group
      of lysine residue

<400> SEQUENCE: 1

```
Arg Gly Asp Phe Lys
1               5

<210> SEQ ID NO 2
<211> LENGTH: 7
<212> TYPE: PRT
<213> ORGANISM: Artificial
<220> FEATURE:
<223> OTHER INFORMATION: heptapeptide, synthetically derived
<220> FEATURE:
<221> NAME/KEY: PEPTIDE
<222> LOCATION: (1)..(7)
<223> OTHER INFORMATION: Binds to NHS-SAM surface through amino group
      of lysine residue

<400> SEQUENCE: 2

Gly Arg Gly Asp Ser Pro Lys
1               5

<210> SEQ ID NO 3
<211> LENGTH: 5
<212> TYPE: PRT
<213> ORGANISM: Artificial
<220> FEATURE:
<223> OTHER INFORMATION: pentapeptide, synthetically derived
<220> FEATURE:
<221> NAME/KEY: PEPTIDE
<222> LOCATION: (1)..(5)
<223> OTHER INFORMATION: Binds to NHS-SAM surface through amino group
      of lysine residue

<400> SEQUENCE: 3

Lys Ala Ala Ala Ala
1               5

<210> SEQ ID NO 4
<211> LENGTH: 5
<212> TYPE: PRT
<213> ORGANISM: Artificial
<220> FEATURE:
<223> OTHER INFORMATION: pentapeptide, synthetically derived
<220> FEATURE:
<221> NAME/KEY: PEPTIDE
<222> LOCATION: (1)..(5)
<223> OTHER INFORMATION: Does not bind to NHS-SAM surface.

<400> SEQUENCE: 4

Arg Gly Asp Gly Gly
1               5
```

METHOD FOR SELECTIVE IMMOBILIZATION OF MACROMOLECULES ON SELF ASSEMBLED MONOLAYER SURFACES

This invention was made with Government support under Contract DE-AC0676RLO-1830 awarded by the U.S. Department of Energy. The Government has certain rights in the invention.

FIELD OF THE INVENTION

The present invention relates generally to molecular deposition, and more particularly, to reactive landing and chemical immobilization of macromolecules on self-assembled monolayer surfaces.

BACKGROUND OF THE INVENTION

Self-Assembled Monolayer (SAM) surfaces (films) form organic interfaces that have properties largely controlled by functional groups (end groups) of molecules that comprise the film. SAM films have useful properties that find applications, e.g., in microcontact printing, in the fabrication of sensors, nanoscale devices, transducers, and patternable materials. Existing techniques for binding macromolecules to SAM surfaces are solution-based synthetic processes that require relatively large quantities of purified materials. New processes are needed that exploit similar chemical reactions but are not solution based to decrease the required quantity of purified materials.

SUMMARY OF THE INVENTION

The present invention is a method for selective chemical binding and immobilization of macromolecules to SAM surfaces. The method includes the steps of: reactively landing the macromolecular ion at a preselected energy from a gas phase to the SAM surface at a preselected location thereon. The SAM surface is attached to a preselected substrate. The attaching group on the macromolecular ion is chemically bound to an attaching (functional) group on the SAM surface, immobilizing the macromolecule on the SAM surface. The invention also includes a method for selective chemical binding of a preselected macromolecule on a SAM surface, characterized by the step of: reactively landing a preselected macromolecule from a gas phase to a preselected location on the SAM surface at a preselected energy location. An attaching group on the macromolecule chemically binds with an attaching group on the SAM surface that immobilizes the preselected macromolecule on the SAM surface. Macromolecules are selected from classes of compounds that include, but are not limited to, e.g., proteins, peptides, dendrimers, polymers, lipids, oligosaccharides, and nucleic acids. In some applications, the macromolecules have a mass-to-charge ratio (m/z) of up to about 4,000. In other applications, macromolecules have a molecular weight up to about 300,000 Daltons. In other applications, the macromolecules have a molecular weight up to about $3.5 \times 10^6$ Daltons. Any reactive SAM surface can be used in conjunction with the invention. Typical reactive SAM surfaces include SAM surfaces that are composed of at least one thiol. Another reactive SAM surface includes SAM surfaces that are composed of at least one silane. Another reactive SAM surface is a carboxylic acid terminated SAM surface (i.e., COOH-SAM) activated with pentafluorophenyl esters or SAM surfaces terminated with an interchain anhydride. Another SAM surface is an N-hydroxysuccinimidyl ester terminated alkylthiol (NHS-SAM) surface on a metal substrate or support. Supports can include any conductive material. Typical metal supports include gold, silver, and metal amalgams that include copper. Supports can also be made of silicon, which is sufficiently conductive. Reactive SAM surfaces further include reactive functional (attaching) groups that include, but are not limited to, e.g., NHS, hydroxyl, carboxylic acid, phosphate, aldehyde, azide, halogen, and other reactive groups. Reactive functional (attaching) groups on the macromolecule include, but are not limited to, e.g., primary amines, aldehydes, carbonyls, alcohols, esters, carboxyls, ornithine, and other reactive functional groups. For example, chemical binding and immobilization of macromolecules such as peptides and proteins on a SAM surface can involve reaction between, e.g., a primary amine group of the lysine residue of a peptide or protein with a terminal NHS group on the SAM surface (i.e., an NHS-SAM surface), which results in release of the NHS moiety and immobilization of the peptide or protein. Reactive landing reactions between a peptide or protein can also be effected using ornithine as the attaching group on the peptide or protein. Saccharides and oligosaccharides can bind to SAM surfaces through reactions that involve a reactive hemiacetal group of the saccharide, which permits reactive landing and immobilization. Nucleic acids or nucleotides can bind to SAM surfaces through electrostatic interactions that involve phosphate groups or through covalent binding of reactive amino groups of the nucleic acid or the nucleotide. Ability to select the location at which binding of macromolecules occurs permits selective positioning, shaping, and patterning of macromolecules on the SAM surface. Shapes on the SAM surface are not limited. For example, reactively landed macromolecular material can have various shapes, which is effected, e.g., in conjunction with shaped apertures in the spectrometer instrument. Shapes include, but are not limited to, ovals (spots), squares, rectangles, and other shapes. In one exemplary test, quantity of macromolecular material immobilized on the SAM surface included a spots with a diameter between about 10 μm and about 10 mm. In another exemplary test, quantity of macromolecular material immobilized on the SAM surface included 1 nanogram of macromolecule in a spot area of 2 mm diameter deposited in about 2 hours. In another exemplary test, quantity of macromolecular material immobilized on the SAM surface included 18 nanograms of macromolecule within a spot area of 5 mm diameter deposited in about 4 hours. Quantity of macromolecular material immobilized on a SAM surface can provide partial coverage or complete coverage. Coverage is preferably selected in the range from about 25% of a monolayer up to about 100% of a monolayer of the macromolecule material on the SAM surface, but is not limited thereto. More preferably, coverage is selected between about 60% and 100% of a monolayer of coverage of the macromolecule material on the SAM surface. Smaller quantities can also be delivered, e.g., down to about 0.1% of a monolayer of coverage of the macromolecule on the SAM surface. Ion currents measured on the substrate for chemical binding of mass-selected macromolecules on SAM surfaces can be selected up to about 10 nA. In other applications, ion currents between about 1 pA and about 600 pA are selected. In yet other applications, ion currents between about 40 pA and about 400 pA are selected. Selective binding provides for controlled preparation of, e.g., protein arrays, which can be further used in conjunction with a peptide or protein array process, or as a component of a protein array device or system. Reactive landing (RL) of mass-selected ions provides several important advantages over existing methods of covalent immobilization of macromolecules: 1)

preparation of 100% pure reactant using mass spectrometry as a preparative separation technique; 2) enhancement of reaction rates by varying kinetic energy of the ion over a broad range during the reactive landing process; 3) patterning of immobilized molecules on substrates. Reactive landing of the invention can be used for controlled preparation of protein arrays. Reactive landing can also be used in preparation of a protein array device or system. Mass spectrometry instrumentation used in conjunction with the invention is not limited. For example, various MS instruments may be utilized, including, but not limited to, Fourier Transform instruments, e.g., Fourier Transform Ion Cyclotron Resonance (FT-ICR) instruments, tandem instruments, time-of-flight (TOF) instruments, ion-trap instruments, e.g., RF- and Paul-ion-trap instruments, quadrupole instruments, sector instruments, e.g., magnetic sector instruments, and combinations thereof. Additionally, various and varied instrumental or MS components may be employed. All instruments and instrument components as will be implemented by those of skill in the art in view of the disclosure are within the scope of the invention.

A more complete appreciation of the invention will be readily obtained by reference to the following description of the accompanying drawings in which like numerals in different figures represent the same structures or elements.

DETAILED DESCRIPTION OF THE INVENTION

The present invention is a method for selective immobilization of macromolecules to self-assembled monolayer (SAM) surfaces that involves reactive landing (RL), or reactive deposition, of macromolecules mass-selected from the gas-phase. The term "reactive landing" refers to any reaction that chemically attaches and immobilizes a mass-selected, gas-phase macromolecule on a SAM surface. SAM surfaces provide a simple and convenient platform for tailoring chemical properties of a variety of substrates. For example, covalent immobilization of macromolecules such as peptides on solid supports plays an important role in biochemistry, with applications ranging from characterization of molecular recognition events at the amino acid level and identification of biologically active motifs in proteins to development of novel biosensors. In addition, gas-phase ion chemistry can be utilized to generate novel compounds that cannot be readily synthesized in solution. Reactive landing chemically binds gas phase macromolecular ions to terminal functional (attaching) groups on the SAM surface or film at preselected locations that results in chemical immobilization of the mass-selected macromolecules on the SAM surface. SAM surfaces that comprise terminal amine, hydroxyl, carboxylic acid, phosphate, aldehyde and halogen groups are susceptible to different classes of organic reactions, such as nucleophilic substitution, esterification, acylation, and nucleophilic addition. Different types of macromolecules including, but not limited to, e.g., peptides, proteins, polymers, lipids, oligosaccharides, and dendrimers can be selectively immobilized on SAM surfaces using low-energy ion-surface collisions. The reactive landing process has been demonstrated using several model peptides reactively landed onto a SAM surface comprising N-hydroxysuccinimidyl ester terminated alkylthiol on gold (NHS-SAM). The method introduces exceptional selectivity and specificity into the surface preparation step by eliminating effects of solvent and sample contamination on the quality of the SAM film. In addition, ability to focus and direct an ion beam at selected spots on the surface with variable sizes allows controllable fabrication of peptide patterns.

Figure 1:
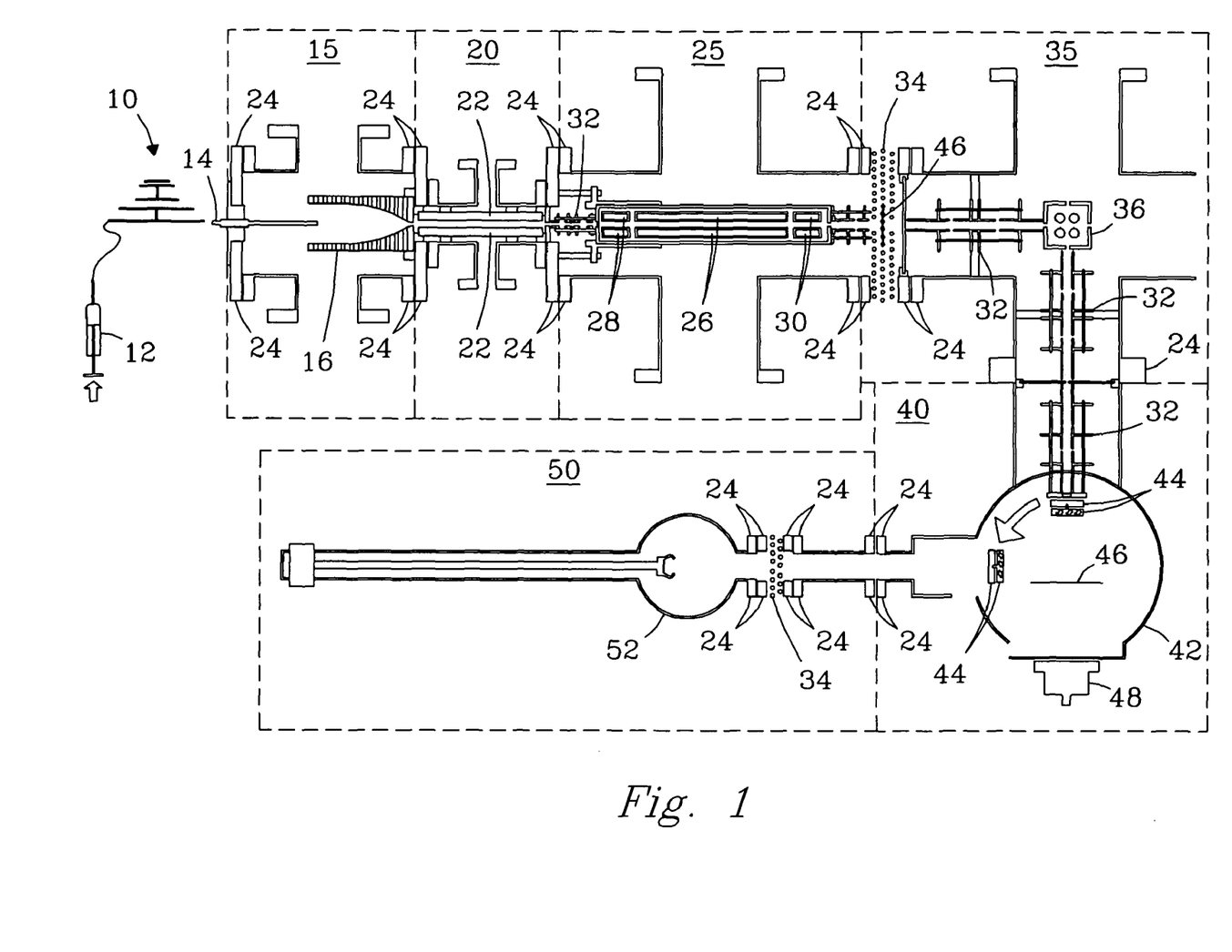
FIG. 1 is a schematic view of an instrument configuration that provides reactive landing for selective chemical immobilization of macromolecules on a SAM surface.

FIG. 1 is a schematic of an instrument described, e.g., by Hadjar et al. (Anal. Chem., 2007, 79, 6566-6574), which reference is incorporated herein in its entirety, that was used for reactive landing (RL) and chemical immobilization of macromolecules on reactive SAM surfaces described herein. In the figure, an ionization (ion) source 10 is illustrated that operates at ambient pressure (e.g. 760 Torr). Ion sources used to generate macromolecular ions are preferably "soft" ion sources, but are not limited. Soft ion sources provide ionization of macromolecules or biomaterials of interest into the gas phase largely intact without a significant loss of signal due to fragmentation. Soft ionization sources include, but are not limited to, electrospray ionization (ESI); matrix-assisted laser desorption/ionization (MALDI); sonic spray ionization; desorption electrospray ionization (DESI); ambient ionization with metastable atoms/ions (DART); atmospheric pressure chemical and photoionization of gases, liquids, or solid samples; corona discharge ionization; fast atom bombardment (FAB) ionization; liquid ionization from droplets (LILBID); field-desorption ionization; laser desorption without a matrix; and combinations thereof. For example, ESI typically produces multiply-protonated (charged) species, e.g., peptides, whereas MALDI predominantly yields singly protonated (charged) species. Macromolecular material is introduced, e.g., via a syringe pump 12 to electrospray ionization (ESI) source 10. Macromolecular ions generated in the ESI ion source are introduced through a heated capillary 14 into the vacuum system of the instrument. The vacuum system of the instrument includes various stages of differential pumping. A first stage of differential pumping 15 includes an ion funnel 16 that operates at a pressure of, e.g., about 0.2 Torr to about 0.5 Torr. A second stage of differential pumping 20 operates at a pressure of, e.g., less than about $10^{-2}$ Torr. Stage 20 includes a collision quadrupole (CQ) 22. Ions exiting the ion funnel undergo collisional relaxation in (CQ) 22, which provides ion thermalization and ion focusing. A conductance limit 24 is positioned at the terminal end of ion funnel 16 and at the terminal end of CQ 22 to maintain pressure in the stage. A third stage of differential pumping 25 operates at a pressure of, e.g., about $1\times10^{-5}$ Torr to about $5\times10^{-5}$ Torr and includes a resolving quadrupole (RQ) 26 that provides for ion mass selection. In the current instrument configuration, RQ 26 is operated in conjunction with a pre-filter 28 and a post-filter 30. Mass-selected ions are transmitted through a series of Einzel lenses 32 positioned at respective ends of stage 25 adjacent to respective conductance limits 24. These lenses enable precise positioning and shaping of the ion beam. A gate valve 34 is positioned after conductance limit 24 (e.g., 2 mm) positioned at the exit end of stage 25. A fourth stage of differential pumping 35 operates at a pressure of, e.g., about $7\times10^{-8}$ Torr to about $1\times10^{-7}$ Torr and includes an electrostatic quadrupole 36 that provides bending (e.g., 90°) of the macromolecular ion beam and also removes unwanted neutral constituents that have potential to contaminate the surface. One or more Einzel lenses 32 are positioned in front of, and behind, quadrupole 36 adjacent to respective conductance limits 24 positioned at the respective ends of stage 35 that provide for selective focusing of the macromolecular ion stream. A fifth stage of differential pumping 40 that includes an ultra high vacuum (UHV) chamber 42 that operates at a pressure of, e.g., about $1\times10^{-9}$ Torr to about $3\times10^{-9}$ Torr. One or more Einzel lenses 32 are positioned within chamber 42 to focus the macromolecular ion beam on the preselected location of the SAM surface 46 introduced to the chamber on a supporting substrate. Prior to RL on SAM surface 46, ions in the ion beam are decelerated, e.g., between deceleration meshes 44, and allowed to reactively land on the SAM surface. Ion collision energy is determined by the difference between the dc offset of the CQ and the potential applied to the surface and the charge state of the ion. Lowering the voltage applied to the surface increases the collision energy for positive ions. As will be understood by those of skill in the art, various equipment components can be coupled to, or introduced to, UHV chamber 42. In the figure, for example, a CCD camera 48 is coupled to UHV chamber 42 that provides visualization of the ion beam prior to deposition on the SAM surface. Visualization enables precise control of the size and position of the ion beam for deposition of single or multiple spots on a SAM surface. Various apertures (not shown) can be positioned to provide selective positioning, shaping, and/or conformation of macromolecular ions on the SAM surface. For example, shapes of reactively landed macromolecules include, but are not limited to, e.g., lines, circles, ovals, squares, rectangles, grids, and other shapes, which permits deposition of macromolecules, e.g., in preparation for use in devices and sensors. Characterization of SAM surfaces following RL provides complementary information on the mode of binding and the quantity of immobilized macromolecules on the SAM surface. SAM surfaces before and after reactive landing can be characterized ex situ, e.g., using time-of-flight secondary-ion mass spectrometry (TOF-SIMS) and Fourier transform (FT) infrared reflection absorption spectroscopy (IRRAS), described further herein. A six stage of differential pumping 50 operates at a pressure of, e.g., about $2\times10^{-8}$ Torr to about $5\times10^{-8}$ Torr and includes a load-and-lock chamber 52 that allows introduction of the SAM surface and supporting substrate into ultra high vacuum chamber 42 without breaking the UHV conditions. A gate valve 34 is positioned between conductance limits 24 of stage 50 and stage 45 provides entry to UHV chamber 42 from load-and-lock chamber 52. Positioning of the SAM surface 46 and its supporting substrate is not limited to UHV chamber 42. For example, the SAM surface and support can be positioned immediately following mass-resolving quadrupole 26 in the intermediate vacuum region of stage 25, which permits greater ion currents at the SAM surface and achieves larger spot sizes. As will be appreciated by those of skill in the art, pressures that provide for reactive landing can vary depending on selected instrument components and instrument configurations. Thus, no limitations are intended. Choice of macromolecule used for reactive landing is limited only by the ionization potential of the mass-selected ion, which is determined, e.g., by the mass-resolving quadrupole of the instrument. Thus, ionization is subject to instrument limitations. For example, in the instant instrument configuration, macromolecules with molecular weights up to about 4000 Daltons can be ionized successfully. Yet, current ionization limits for mass-selected macromolecules is considered to be about $3.5\times10^{6}$ Daltons. Further theoretical ionization limits are considered to be possible. Thus, all macromolecules that can be ionized fall within the scope of the invention. Quantity (ion dose) of macromolecular ions delivered to a surface can be estimated and controlled by monitoring ion current at the surface. Ion currents up to about 10 nanoamperes (nA) are feasible. Typical ion currents of mass-selected ions delivered to a surface range from several picoamperes (pA) to several nanoamperes, which correspond with a deposition of from about 0.1 ng to about 100 ng of macromolecular material in 1 h for molecules with a molecular weight of about 1000 Daltons (amu). In a typical instrument setup, at 40 eV collision energy, mass-selected and doubly charged peptide ions delivered to a surface positioned after the mass-resolving quadrupole exhibit an optimized current of ~400 pA. Consequently, different deposition times are used to obtain similar ion doses at different collision energies.

Figure 2:
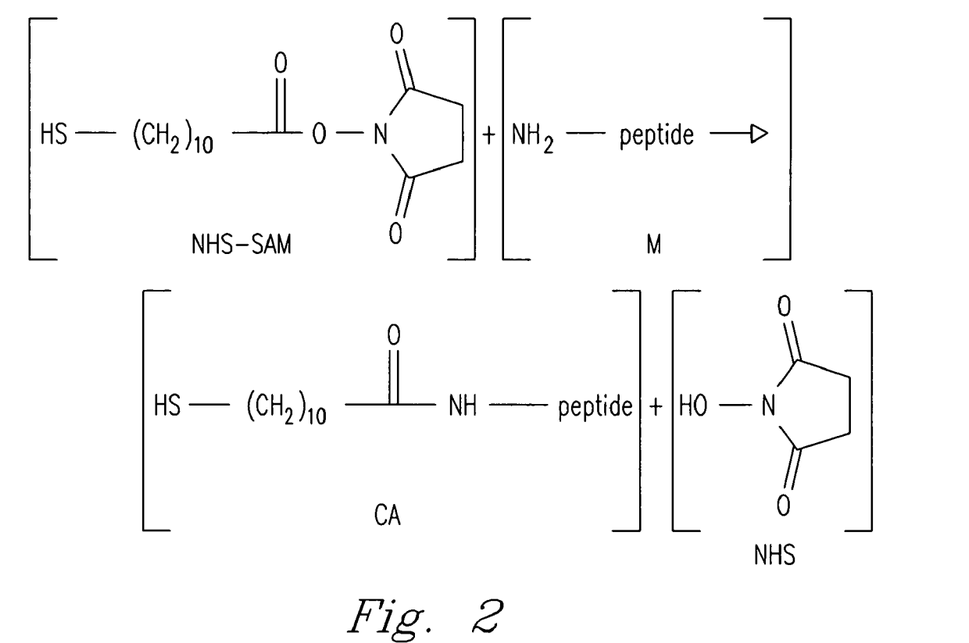
FIG. 2 illustrates a reaction process for chemical immobilization of an exemplary macromolecule on an NHS-SAM surface.

FIG. 2 illustrates a generalized chemical process for chemical binding and thus immobilization of macromolecules on an exemplary NHS-SAM surface comprised of N-hydroxysuccinimidyl (NHS) ester-terminated alkylthiols (NHS-SAM). In the figure, the NHS-SAM surface reacts with an accessible primary amine group, e.g., of a lysine residue, of the mass-selected macromolecules, here shown as a peptide (M) or a protein (M), which is then immobilized on the SAM surface by formation of amide bonds. The amine group on the peptide selectively binds with the N-hydroxysuccinimidyl (NHS) ester group on the NHS-SAM surface resulting in formation of a chemical adduct (CA) comprising an amide bond between the amine group of the peptide and the carbonyl group of on the NHS-SAM surface, with an accompanying release of N-hydroxysuccinimide (NHS). In general, peptides can be covalently linked to NHS-SAM surfaces via an N-terminal a-amino group or an E-amino group of a lysine side chain. Although other residues such as arginine and histidine also have an amino group in the side chain, they do not react with NHS esters. Macromolecules containing ornithine side chains are also reactive. Electrostatic binding is also possible between, e.g., phosphate groups of nucleic acids and positively charged SAM surfaces. In an exemplary system, cyclic pentapeptide, i.e., c(-RGDfK-) (SEQ. ID. NO: 1) where (f=D-phenylalanine), and a NHS-SAM surface were used. In this system, the cyclic peptide c(-RGDfK-) lacks an N-terminal amine group. Formation of the amide bond is thus between an ϵ-amino group of a lysine side chain of the gas phase peptide and the N-hydroxysuccinimidyl (NHS) ester group on the NHS-SAM surface. Reactive landing (RL) results in efficient covalent chemical binding of the mass-selected macromolecule. Peptides immobilized through RL are strongly bound to the surface and are not removed by sonication or rinsing with solvents. Reaction yield is also independent of the charge state of the (mass-selected) projectile ions, indicating complete or partial neutralization of incident ions-upon collision with the SAM surface. While chemical immobilization of macromolecules is described herein in reference to peptides, the invention is not limited thereto. As will be understood by those of skill in the chemical arts, all classes of macromolecular ions that bind to surface functional groups and that can be ionized and mass-selected in the gas-phase, can be utilized by the process of the invention. All such macromolecules are within the scope of the invention. Thus, no limitations are intended.

Figure 3:
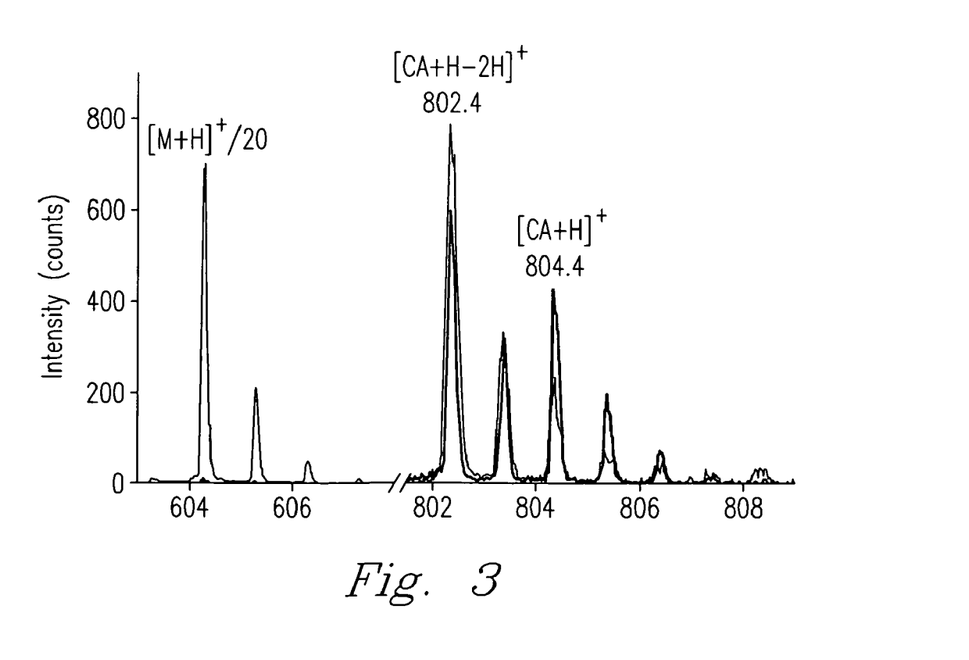
FIG. 3 presents TOF-SIMS spectra of an NHS-SAM surface following reactive landing of an exemplary pentapeptide, c(-RGDfK-) (SEQ. ID. NO: 1).

FIG. 3 presents a TOF-SIMS spectrum of NHS-SAM surface following RL of c(-RGDfK-) (SEQ. ID. NO: 1) ions which shows several peptide-related peaks. The TOF-SIMS spectrum is dominated by peaks corresponding to singly protonated macromolecular ions (M), i.e., $[M+H]^+$ ions, identified, e.g., at an (m/z) value of 604.3 eV. These ions are not bound to the surface and thus are readily removed following rinsing. A number of peptide-related peaks are not affected by sonication or rinsing, indicative of peptide molecules that are chemically (covalently) bound to the NHS-SAM surface. Peaks corresponding to covalently bound adducts (CA) without the NHS endgroup, i.e., $[CA+H-2H]^+$ and $[CA+H]^+$, are identified at (m/z) values of 802.4 and 804.4, respectively. The covalent adduct $[CA+H-2H]^+$ is an analog of $[CA+H]^+$ and has an additional double bond. This doublet pair is an important signature of the covalent binding through formation of the amide bond. A covalent adduct is also observed at an (m/z) value of 1000.4 (not shown) corresponding to the macromolecular ion cationized on gold, i.e., $[CA+Au]^+$. Various CA fragment ions are also formed corresponding to loss of $H_2S/S$ from the doublet and $[CA+Au]^+$ followed by subsequent losses of $CH_2$ groups from the thiol chain (not shown). Further fragmentation proceeds via loss of NHCO moieties followed by loss of additional $CH_2$ groups from the side chain of the lysine residue. Observed fragmentation patterns provide evidence of covalent binding of the c(-RGDfK-) peptide (SEQ. ID. NO: 1) to the NHS-SAM surface through the lysine side chain. Other lysine-containing synthetic peptides including, e.g., GRGDSPK (SEQ. ID. NO: 2) and KAAAA (SEQ. ID. NO: 3), exhibit similar doublet peaks, albeit at different m/z values, demonstrating successful RL, chemical binding, and immobilization to the NHS-SAM surface. Although gold is a preferred support material, SAM surfaces can also be constructed on supports and substrates other than gold. Any metal can be used that is sufficiently conductive. In addition, supports comprising single metals as well as supports comprising metal amalgams doped with copper are suitable for use. Silicon as a support also provides sufficient conduction to be used. Silicon is a preferred support for SAM surfaces composed of silanes. SAM surfaces composed of silanes are suitable for use in conjunction with the invention when constructed with terminal reactive functional groups that are available on the surface.

Figure 4:
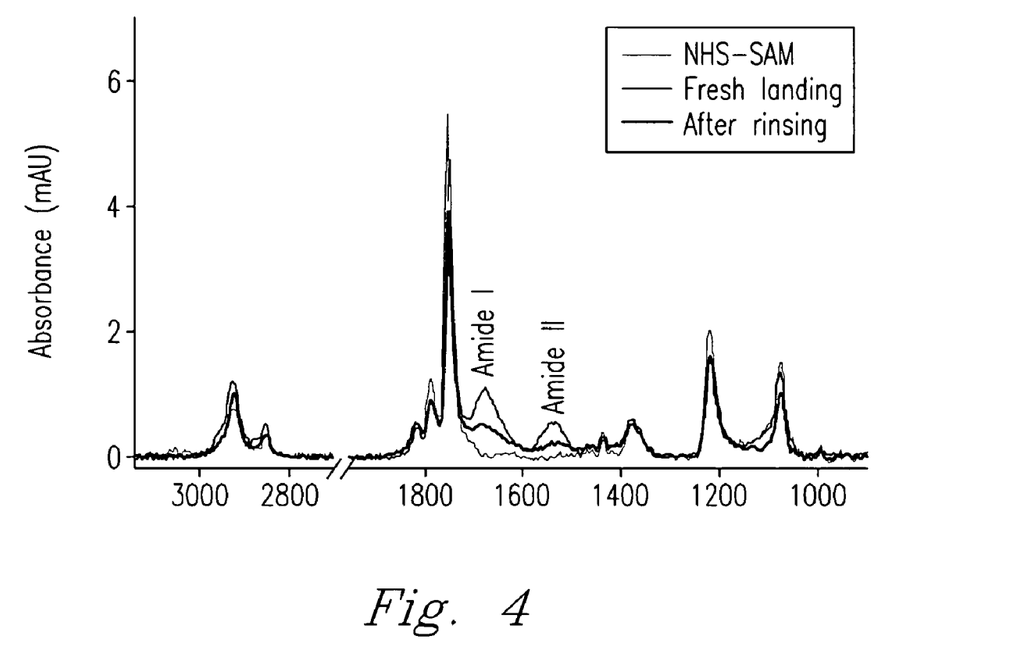
FIG. 4 presents IRRAS spectra of an NHS-SAM surface following reactive landing of an exemplary pentapeptide, c(-RGDfK-) (SEQ. ID. NO: 1), and following rinsing.

FIG. 4 presents Fourier transform (FT) infrared reflection absorption spectroscopy (IRRAS) spectra for an unmodified NHS-SAM surface prior to RL, following 4 hr RL of ~18 ng of c(-RGDfK-) (SEQ. ID. NO: 1) ions, and following extensive sonication and rinsing in methanol. In the figure, characteristic amide bands are observed at 1676 $cm^{-1}$ (Amide 1) and 1535 $cm^{-1}$ (Amide 2) following RL of c(-RGDfK-) on the NHS-SAM surface. Subsequent rinsing of the surface reduces intensity of the amide bands by a factor of 2, indicating that about half of the observed IRRAS signal corresponds to species that are loosely bound to the surface. Covalent attachment of the peptides to the surface also results in suppression of bands characteristic of the NHS endgroup that include the asymmetric stretch of the NHS carbonyls at 1751 $cm^{-1}$, the asymmetric CNC stretch of the NHS at 1216 $cm^{-1}$ and the NCO stretch of the NHS at 1074 $cm^{-1}$, respectively. Other lysine-containing peptides including, e.g., GRGDSPK (SEQ. ID. NO: 2) and KAAAA (SEQ. ID. NO: 3), exhibit similar peaks demonstrating successful RL, chemical binding, and immobilization to the NHS-SAM surface.

Figure 5:
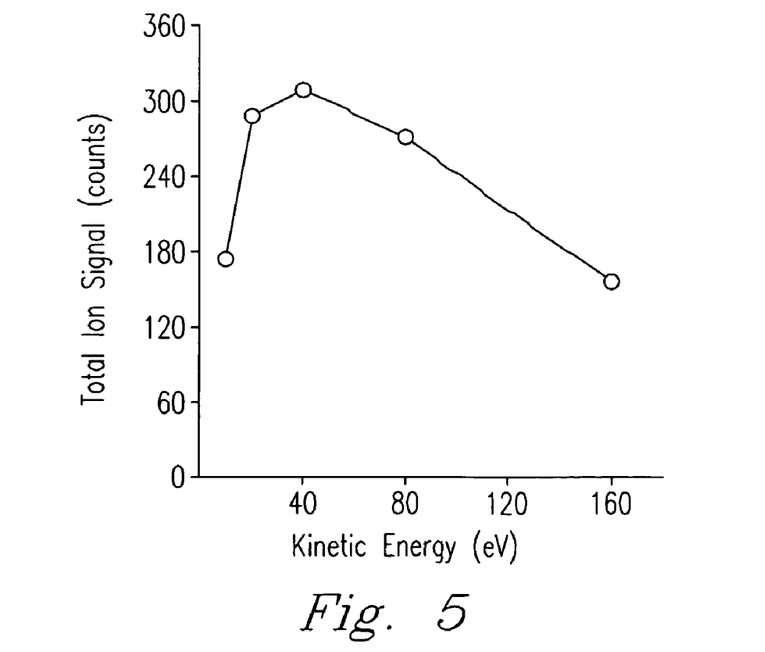
FIG. 5 is a plot showing total ion signal at an NHS-SAM surface as a function of collision energy.

FIG. 5 is a plot of the total covalent adduct (CA) ion signal as a function of the kinetic energy of the projectile ion. Chemical binding reactions involving mass-selected macromolecular ions take place upon reactive landing with the surface, which reactions are promoted by the kinetic (collision) energy of the ion. Kinetic (collision) energies of projectile ions facilitate reactivity on the SAM surface. Effect of initial kinetic energy of the projectile ion on the efficiency of the reactive landing was investigated by comparing reaction yields following deposition of doubly protonated c(-RGDfK-) (SEQ. ID. NO: 1) ions onto NHS-SAM surfaces over a wide range of collision energies ($10^{-160}$ eV). The plot shows the dependence of reaction efficiency on collision energy. Results show that kinetic energy of the ion must be sufficiently high (>10 eV) to overcome any reaction barrier, but low enough (<150 eV) to prevent dissociation of the ion during collision. In the figure, ion signal (and thus reaction yield) shows a gradual increase at collision energies below 20 eV, followed by a plateau region from 20 to 80 eV, and a decrease at collision energies above 100 eV. Results indicate that at high collision energies, chemical binding reactions are determined by efficiency of reactive landing and ion trapping on the surface. In particular, the slow decrease in fraction of ions trapped on the surface occurs with an increase in collision energy between 0 and 100 eV, followed by a fairly sharp decrease observed at energies above 100 eV. In contrast, at lower collision energies where RL efficiency shows no significant dependence on collision energy, kinetic energy of projectile ions overcomes any reaction barrier. As a result, RL efficiency increases with collision energy. The observed pattern is attributed to competition between RL and scattering of ions at higher collision energies. In another example involving a peptide with sequence GRGDSPK (SEQ. ID. NO: 2), only a small amount of GRGDSPK could be grafted onto the NHS-SAM surface after 15 hrs of reaction in solution. In contrast, a significant amount of the peptide was covalently immobilized on the surface following reactive landing. In this experiment, the surface was irradiated for 4 hrs using a 400 pA beam of mass-selected ions focused onto a 5 mm spot. Comparison between IRRAS spectra obtained following the solution phase reaction and reactive landing demonstrated that the local coverage of GRGDSPK on the NHS-SAM surface obtained after 4 hr of reactive landing is ca. 4 times greater than the local coverage obtained after 15 hrs of reaction in solution. Comparison between the reactivity of the GRGDSPK peptide with the NHS-SAM surface in solution and in the gas phase suggests that relatively high kinetic energy of projectile ions utilized in RL experiments can promote reactions on surfaces that are characterized by very slow kinetics in solution. Presumably, ion-surface collision results in a local heating of the surface that facilitates the reactivity. A unique advantage of surface modification using RL is the ability to control the kinetic energy of projectile ions that is essential for overcoming any reaction barrier. RL yield does not increase with longer contact times, suggesting that desired immobilization (covalent binding) reactions take place during collision. RL efficiency does not show any significant dependence on peptide composition. Reaction yield is also independent of the charge state of the projectile ions, suggesting that peptide ions undergo efficient neutralization upon collision. For example, reaction yield for the landing of c(-RDGfK-) (SEQ. ID. NO: 1) onto an NHS-SAM surface is independent of the charge state of the precursor ion indicating these peptide ions undergo efficient neutralization upon collision with the SAM surface. Reactive landing is strongly affected by presence and availability of specific chemical functional groups necessary for covalent binding, e.g., SAM surfaces which are activated with a labile NHS ester terminal group. Efficiency of reactive landing (RL) is a function of the reaction between the terminal functional group on the SAM surface and reactive functional groups of the macromolecular ion. For example, efficient formation of amide bonds between peptides and active ester terminated NHS-SAM surfaces is observed for peptides that contain the lysine residue. Reaction efficiency with primary amino groups of peptides can also be improved using carboxylic acid terminated SAM surfaces (i.e., COOH-SAM) activated with pentafluorophenyl esters or SAM surfaces terminated with an interchain anhydride. Activation of a COOH-SAM surface with an NHS group also expedites reaction of the monolayer with amine-containing molecules. Physical properties of the SAM surface also influence reactivity at the interface including, e.g., the organization of the chains in the monolayer, density and orientation of functional groups on the surface, and lateral steric effects.

CONCLUSIONS

A novel approach has been described for controlled immobilization of macromolecules to SAM surfaces using RL of the mass-selected macromolecular ions. Efficient covalent linkage of peptide ions to an NHS-SAM surface has been demonstrated through the lysine side chain. Similar local surface coverage is achieved using 4 hr RL that compares with 2 hr solution-phase reaction for a cyclic RGDfK peptide (SEQ. ID. NO: 1) and 4 times higher coverage was obtained for a linear GRGDSPK peptide (SEQ. ID. NO: 2) using 4 hr RL as compared to 15 hr of reaction in solution High selectivity and specificity inherent to mass spectrometry and ion beam chemistry provide unprecedented control for preparation of novel substrates for biorecognition studies and biomaterials for stimulated protein and cell adhesion. Reactive landing of mass-selected and energy-selected peptide ions onto SAM surfaces has several unique advantages for the covalent immobilization of peptides as compared to the conventional approaches that utilize solution-phase chemistry. It introduces exceptional selectivity and specificity into the surface preparation step by eliminating the effect of solvent and sample contamination on the quality of the film. In addition, the shaping and precise positioning of the ion beam on the surface enables selective modification of specific areas on the substrate which could be utilized for patterning of the SAM surfaces. The following Examples are intended to provide a further understanding of various aspects of the invention.

EXAMPLE 1

Preparation of NHS-SAM Target Surface

Dithiobis succinimidyl undecanoate (i.e., dithiobis) (Dojindo Molecular Technologies, Gaithersburg, Md.) and 11-mercaptoundecanoic acid (Sigma-Aldrich, St. Louis, Mo.) were used. Self-assembled monolayers of N-hydroxysuccinimidyl ester (NHS-SAM) and 11-mercaptoundecanoic acid (COOH-SAM) were prepared using modified procedures detailed, e.g., by Wagner et al. (Biophys. J., 1996, 70, 2052) and Wang et al. (Langmuir, 2005, 21, 2633). 10×10 mm gold-coated silicon wafers with a 100 nm gold layer deposited on top of a 10 nm chromium adhesion layer (SPI Supplies, West Chester, Pa.) were thoroughly cleaned in an ultraviolet ozone cleaner and immersed in 1 mM solutions of the corresponding thiols in ethanol (20% v/v methylene dichloride was added to increase solubility of dithiobis) for 12 h. Substrates were removed from the thiol solution, ultrasonically washed in ethanol (10% v/v acetic acid in ethanol was used for the COOH-SAM) to remove physisorbed molecules from the SAM surface, and dried under nitrogen beam.

EXAMPLE 2

Reactive Landing of Mass Selected Macromolecular Ions

Experiments were conducted using a RL instrument described herein. Various synthetic peptides were dissolved for use in a 50:50 (v/v) methanol-water solution containing 1% acetic acid to a concentration of ~0.1 mM that gave a maximum ion current on the SAM surface. Singly (m/z value: 604.3) and doubly (m/z value: 302.7) protonated ions of c(-RGDfK-) (SEQ. ID. NO: 1) (f=D-phenylalanine) were produced in an electrospray ionization (ESI) source. Ions were introduced into the vacuum system using an electrodynamic ion funnel that was efficiently focused in a collisional quadrupole. Ions were mass selected using a commercial quadrupole mass filter. Mass-selected ions were transferred to an NHS-SAM surface through an electrostatic bending quadrupole and a series of Einzel lenses that enabled shaping and positioning of the ion beam. Current of mass-selected ions delivered to the surface was, e.g., 40 pA corresponding to a deposition of ~1 ng of c(-RGDfK-) onto a 2 mm spot in ~2 hours. Samples with larger spot size were prepared, e.g., by placing the reactive landing target after the resolving quadrupole. This allowed deposition of ~18 ng of peptide onto a 5 mm spot by exposing the NHS-SAM surface to a 400 pA ion beam for 4 hours. Local coverage was about 60% of a monolayer. RL of other macromolecular peptide ions, e.g., doubly protonated GRGDSPK (SEQ. ID. NO: 2) (m/z 358.7); and singly protonated RGDGG (SEQ. ID. NO: 4) (m/z 461.2) ions gave similar results.

We claim:

1. A method for selective chemical binding of a preselected macromolecule, characterized by the steps of:
   reactively landing a selected macromolecule having a reactive group from a gas phase to a preselected location on a self-assembled monolayer (SAM) surface having an attaching group capable of reacting with the reactive group at a preselected energy between 10 eV and 150 eV per charge;
   chemically binding said preselected macromolecule with the attaching group on said SAM surface; and
   immobilizing said preselected macromolecule on said SAM surface.

2. The method of claim 1, wherein the step of reactively landing includes a macromolecule selected from the group consisting of: proteins, peptides, dendrimers, lipids, polymers, oligosaccharides, and nucleic acids.

3. The method of claim 2, wherein said macromolecule has an m/z value up to about 4,000.

4. The method of claim 2, wherein said macromolecule has a molecular weight up to about $3.5 \times 10^6$ Daltons.

5. The method of claim 1, wherein the step of reactively landing said preselected macromolecule includes a chemical reaction with an attaching group on said SAM surface selected from the group consisting of: NHS, hydroxyl, carboxylic acid, phosphate, aldehyde, azide, halogen, and combinations thereof.

6. The method of claim 1, wherein the step of reactively landing said preselected macromolecule includes at least one reactive group on said macromolecule selected from the group consisting of: a primary amine, an aldehyde, a carbonyl, an alcohol, an ester, a carboxyl, ornithine, and combinations thereof.

7. The method of claim 1, wherein said SAM surface is a SAM surface composed of at least one thiol.

8. The method of claim 1, wherein said SAM surface is a SAM surface composed of at least one silane.

9. The method of claim 1, wherein said SAM surface is an N-hydroxysuccinimidyl ester terminated alkylthiol (NHS-SAM) surface on a metal substrate.

10. The method of claim 1, wherein said SAM surface is a carboxylic acid terminated SAM surface (COOH-SAM) activated with pentafluorophenyl ester, or a SAM surface (COOH-SAM) terminated with an interchain anhydride.

11. The method of claim 1, wherein the step of reactively landing said preselected macromolecule includes shaping or patterning said preselected macromolecule on said SAM surface.

12. The method of claim 1, wherein the step of reactively landing said preselected macromolecule includes selectively positioning said preselected macromolecule on said SAM surface.

13. The method of claim 1, wherein the step of reactively landing said preselected macromolecule includes forming a spot of said macromolecule on said SAM surface with a diameter between about 100 µm and about 10 mm.

14. The method of claim 1, wherein the step of reactively landing said preselected macromolecule includes an on current up to about 10 nA.

15. The method of claim 1, wherein the step of reactively landing said preselected macromolecule includes an on current in the range from about 1 pA to about 600 pA.

16. The method of claim 1, wherein the step of reactively landing said preselected macromolecule includes an ion current in the range between about 40 pA and about 400 pA.

17. The method of claim 1, wherein the step of reactively landing said preselected macromolecule deposits about 1 nanogram of said macromolecule in about 2 hours to a spot on said SAM surface that is about 2 millimeters in diameter.

18. The method of claim 1, wherein the step of reactively landing said preselected macromolecule deposits about 18 nanograms of said macromolecule in about 4 hours to a spot on said SAM surface that is about 5 millimeters in diameter.

19. The method of claim 1, wherein the step of reactively landing said preselected macromolecule provides between about 0.1% and about 60% of a monolayer of coverage of said macromolecule on said SAM surface.

20. The method of claim 1, wherein the step of reactively landing said preselected macromolecule provides at least about 60% of a monolayer of coverage of said macromolecule on said SAM surface.

21. The method of claim 1, wherein the step of reactively landing said preselected macromolecule provides at least about 80% of a monolayer of coverage of said macromolecule on said SAM surface.

22. The method of claim 1, wherein the step of reactively landing said preselected macromolecule provides up to about 100% of coverage of said macromolecule on said SAM surface.

23. The method of claim 1, wherein the step of reactively landing said preselected macromolecule provides coverage on said SAM surface that is partial.

24. The method of claim 1, wherein the step of reactively landing said preselected macromolecule provides coverage on said SAM surface that is complete.

25. The method of claim 1, wherein the step of reactively landing said preselected macromolecule includes a reaction between a primary amine group of a peptide with an attaching group on said SAM surface.

26. The method of claim 1, wherein said method is used for controlled preparation of a protein array, wherein preparation of the protein array comprises the steps of:
    ionizing a preselected protein macromolecule;
    transferring the protein macromolecule in an ion beam into a mass analyzer;
    mass-selecting a charge state for a preselected mass-to-charge ratio of interest for the preselected protein macromolecule; and
    orienting the SAM surface at a suitable angle with respect to the axis of the ion beam containing the charge state of the preselected protein macromolecule before reactively landing same at the preselected location on the SAM surface at the preselected energy.

* * * * *

UNITED STATES PATENT AND TRADEMARK OFFICE
CERTIFICATE OF CORRECTION

PATENT NO. : 8,067,053 B2  
APPLICATION NO. : 12/151945  
DATED : November 29, 2011  
INVENTOR(S) : Julia Laskin and Peng Wang Page 1 of 1

It is certified that error appears in the above-identified patent and that said Letters Patent is hereby corrected as shown below:

Col. 13, line 21: replace "on" with "ion"

Col. 13, line 24: replace "on" with "ion"

Signed and Sealed this  
Seventeenth Day of January, 2012

David J. Kappos  
*Director of the United States Patent and Trademark Office*